(12) United States Patent
Rush et al.

(10) Patent No.: US 8,282,578 B2
(45) Date of Patent: Oct. 9, 2012

(54) INTEGRATED LANCET AND ANALYTE TESTING APPARATUS

(75) Inventors: Benjamin M. Rush, Oakland, CA (US); Benjamin J. Feldman, Oakland, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 376 days.

(21) Appl. No.: 12/572,953

(22) Filed: Oct. 2, 2009

(65) Prior Publication Data

US 2010/0087754 A1    Apr. 8, 2010

Related U.S. Application Data

(60) Provisional application No. 61/102,640, filed on Oct. 3, 2008.

(51) Int. Cl.
| | |
|---|---|
| *A61B 5/00* | (2006.01) |
| *A61B 17/32* | (2006.01) |
| *B65D 81/00* | (2006.01) |
| *C12M 1/00* | (2006.01) |

(52) U.S. Cl. ........ 600/584; 600/583; 606/181; 606/182; 606/183; 606/185; 204/403.01

(58) Field of Classification Search ............. 204/403.01; 600/583, 584; 606/181, 182, 183, 185
See application file for complete search history.

(56) References Cited

U.S. PATENT DOCUMENTS

| | | | | |
|---|---|---|---|---|
| 5,510,266 | A | * | 4/1996 | Bonner et al. ............... 436/43 |
| 6,027,459 | A | * | 2/2000 | Shain et al. ................ 600/573 |
| 6,071,251 | A | * | 6/2000 | Cunningham et al. ...... 600/584 |
| 6,143,164 | A | | 11/2000 | Heller et al. |
| 6,206,841 | B1 | * | 3/2001 | Cunningham et al. ...... 600/584 |
| 6,283,982 | B1 | | 9/2001 | Levaughn et al. |
| 6,506,168 | B1 | * | 1/2003 | Fathallah et al. ........... 600/578 |
| 6,592,745 | B1 | | 7/2003 | Feldman et al. |
| 6,616,819 | B1 | | 9/2003 | Liamos et al. |
| 7,566,419 | B2 | * | 7/2009 | Schulat et al. ............. 422/68.1 |
| 7,922,971 | B2 | * | 4/2011 | Bryer et al. ................. 422/50 |
| 2002/0169393 | A1 | * | 11/2002 | Cunningham et al. ...... 600/573 |
| 2003/0191415 | A1 | * | 10/2003 | Moerman et al. .......... 600/584 |
| 2003/0212345 | A1 | * | 11/2003 | McAllister et al. ......... 600/584 |
| 2004/0064068 | A1 | * | 4/2004 | DeNuzzio et al. .......... 600/583 |
| 2004/0138588 | A1 | * | 7/2004 | Saikley et al. .............. 600/583 |
| 2005/0015020 | A1 | * | 1/2005 | LeVaughn et al. .......... 600/583 |
| 2005/0240119 | A1 | * | 10/2005 | Draudt et al. ............... 600/583 |
| 2006/0025662 | A1 | | 2/2006 | Buse et al. |
| 2006/0091006 | A1 | | 5/2006 | Wang et al. |
| 2006/0161078 | A1 | * | 7/2006 | Schraga ....................... 600/583 |
| 2007/0007183 | A1 | * | 1/2007 | Schulat et al. ............... 209/573 |
| 2007/0068807 | A1 | | 3/2007 | Feldman et al. |
| 2007/0088377 | A1 | * | 4/2007 | LeVaughn et al. ........... 606/181 |
| 2007/0095661 | A1 | | 5/2007 | Wang et al. |
| 2007/0108048 | A1 | | 5/2007 | Wang et al. |
| 2007/0199818 | A1 | | 8/2007 | Petyt et al. |
| 2008/0066305 | A1 | | 3/2008 | Wang et al. |
| 2008/0102441 | A1 | | 5/2008 | Chen et al. |

(Continued)

*Primary Examiner* — Sean Dougherty
(74) *Attorney, Agent, or Firm* — Edward J. Baba; Daniel G. Stoddard; Bozicevic, Field & Francis LLP

(57) ABSTRACT

Integrated lancing and analyte measurement systems are provided which minimize the number of actions required to operate the systems, accomplished in part by combining two or more user steps into one.

33 Claims, 11 Drawing Sheets

U.S. PATENT DOCUMENTS

| | | |
|---|---|---|
| 2008/0114280 A1 | 5/2008 | Stafford |
| 2008/0119702 A1 | 5/2008 | Reggiardo |
| 2008/0119710 A1 | 5/2008 | Reggiardo |
| 2008/0119760 A1* | 5/2008 | Lok et al. .................. 600/583 |
| 2008/0148873 A1 | 6/2008 | Wang |
| 2008/0190766 A1* | 8/2008 | Rush et al. ................. 204/400 |
| 2008/0200782 A1* | 8/2008 | Planman et al. ............ 600/316 |
| 2008/0267823 A1 | 10/2008 | Wang |
| 2009/0005664 A1* | 1/2009 | Freeman et al. ............ 600/347 |
| 2009/0048536 A1* | 2/2009 | Freeman et al. ............ 600/583 |
| 2009/0105570 A1 | 4/2009 | Sloan et al. |
| 2009/0143701 A1* | 6/2009 | Ghesquiere et al. ........ 600/583 |

* cited by examiner

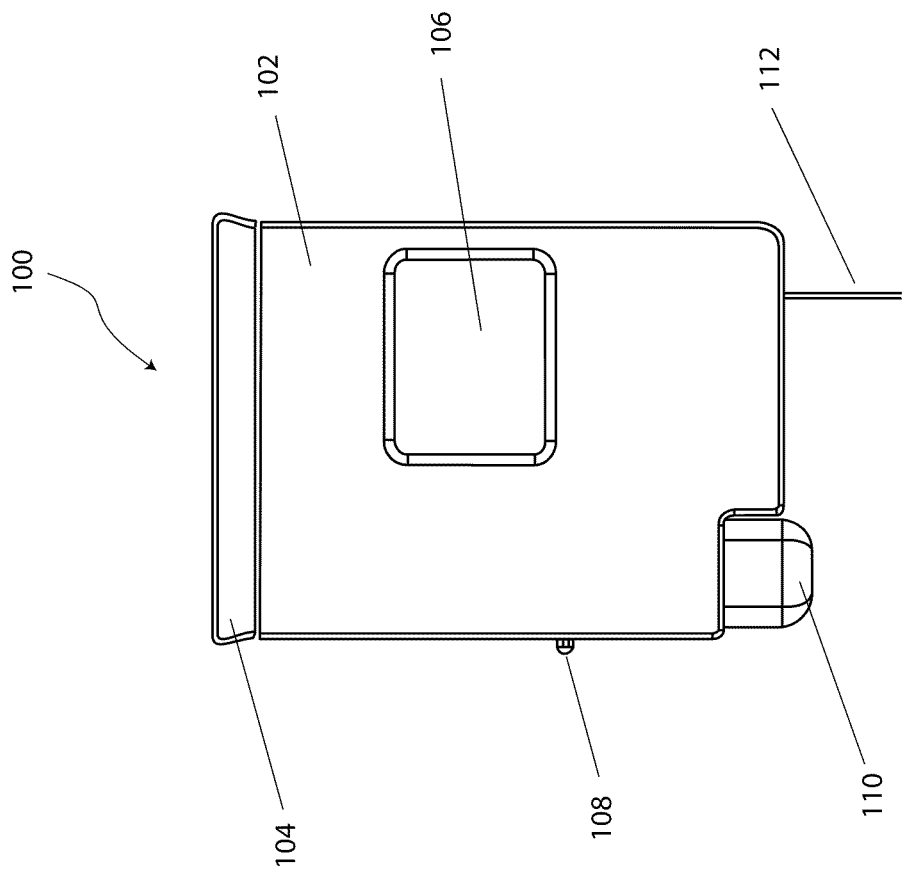
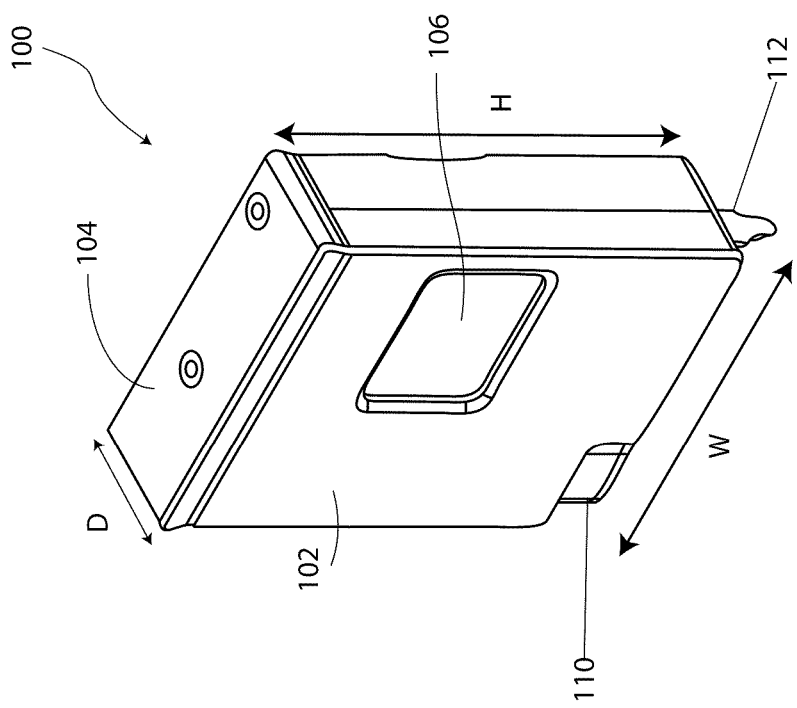
FIG. 1B
FIG. 1A

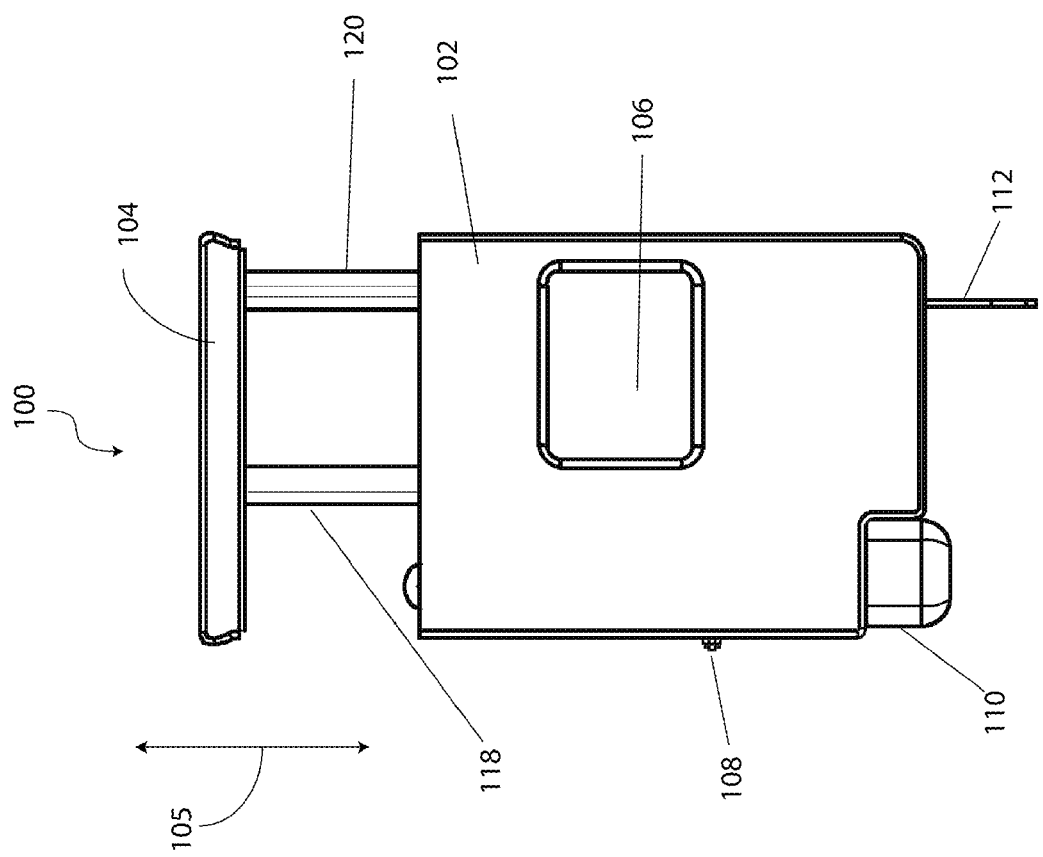
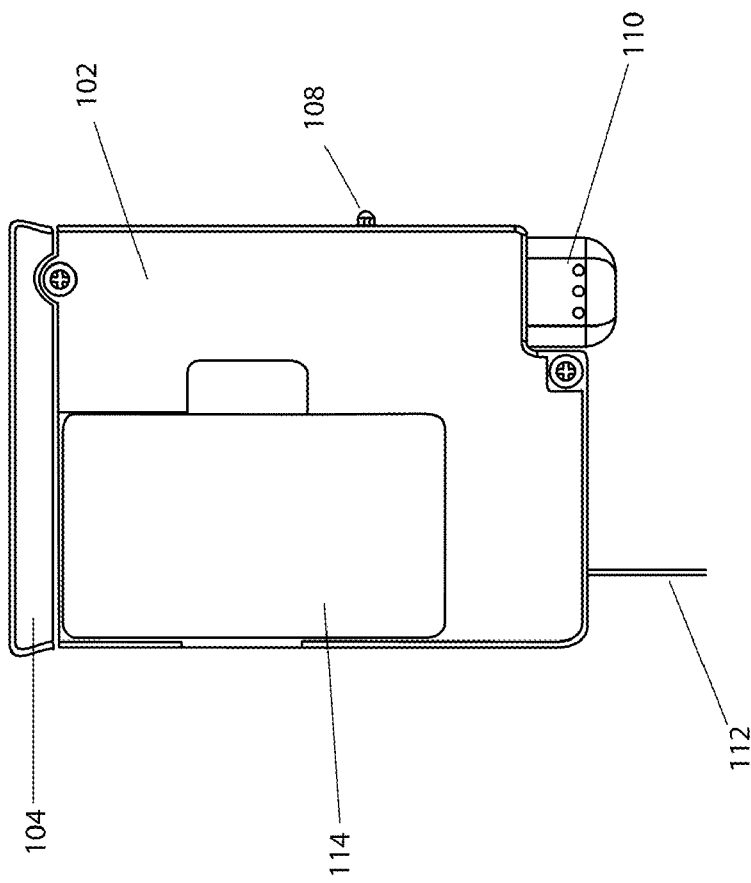
FIG. 2A
FIG. 1C

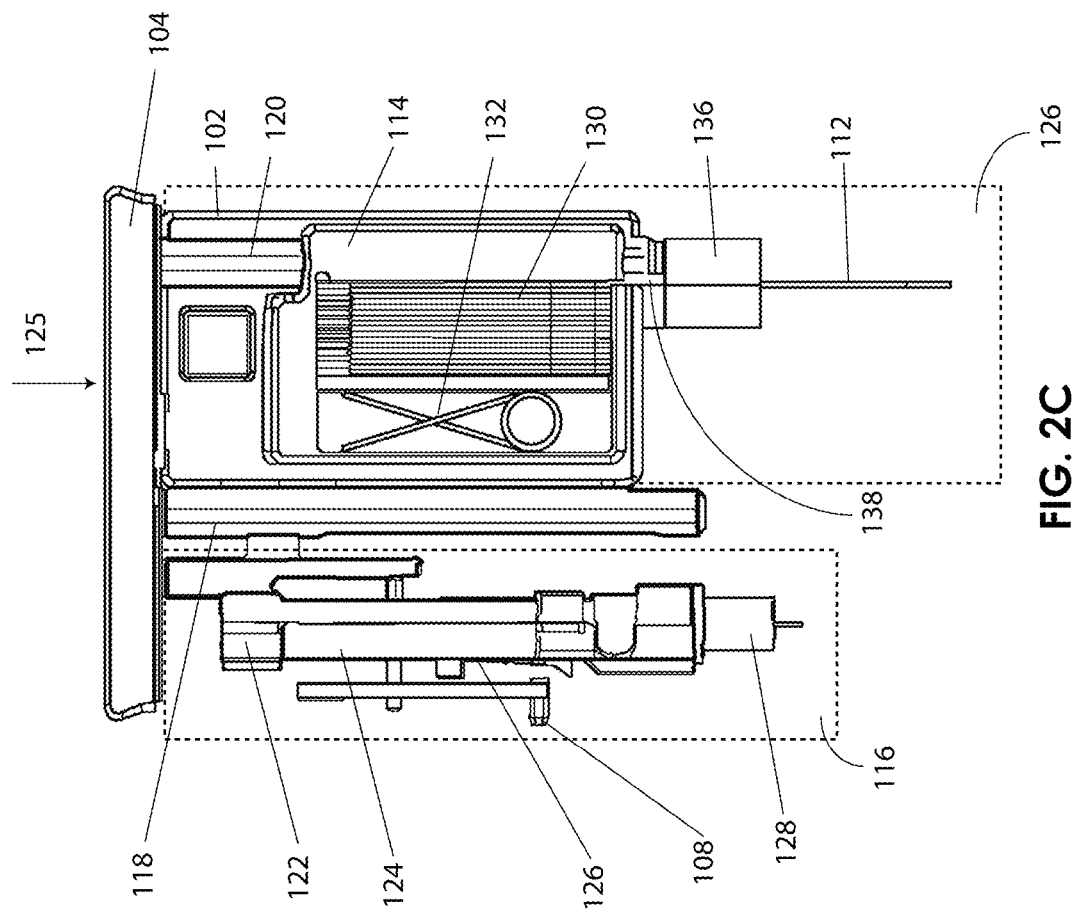
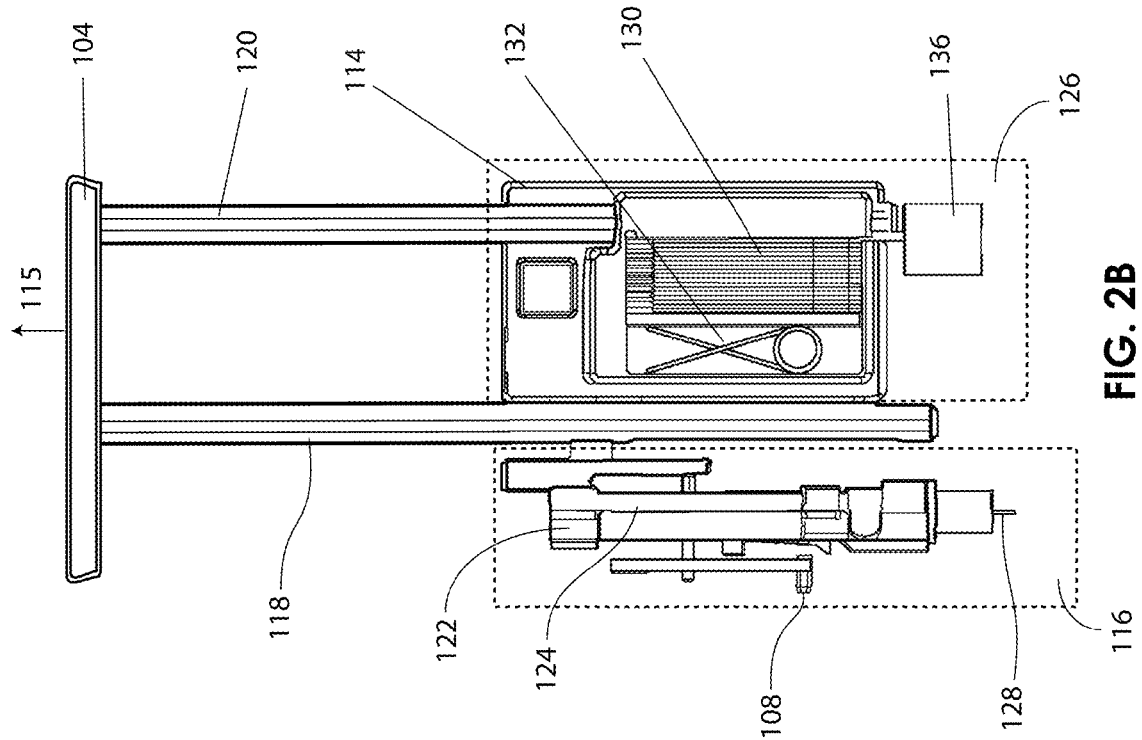
FIG. 2B
FIG. 2C

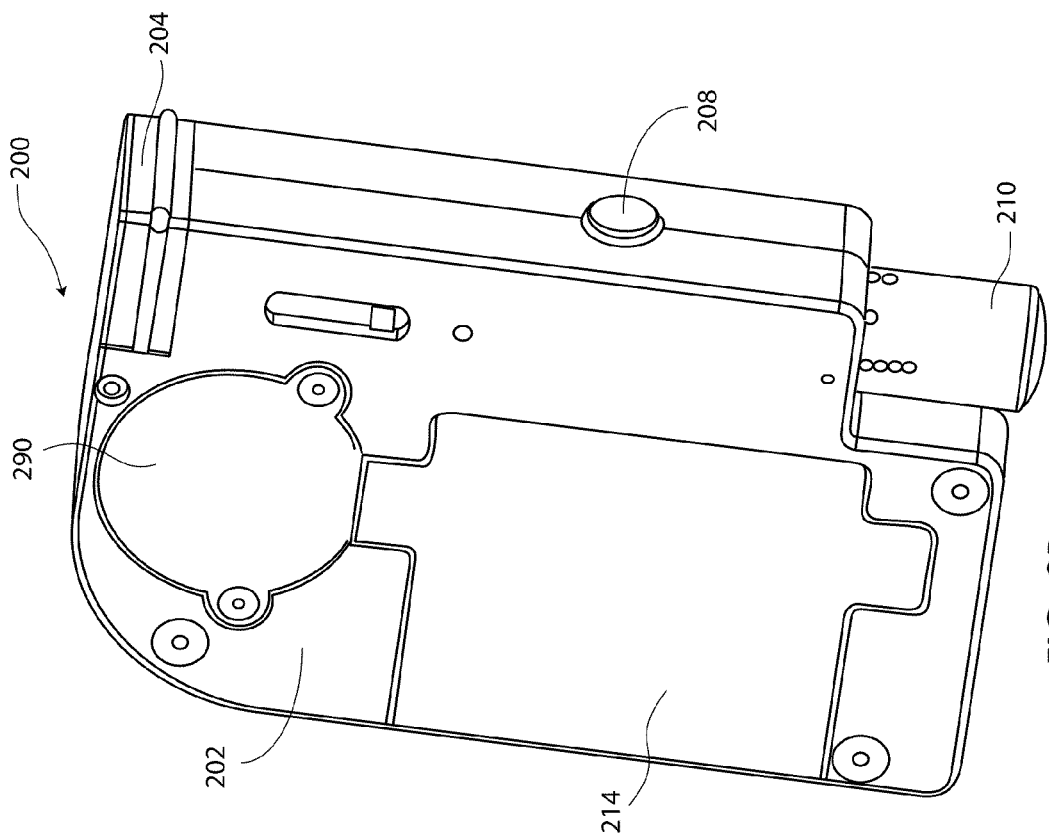
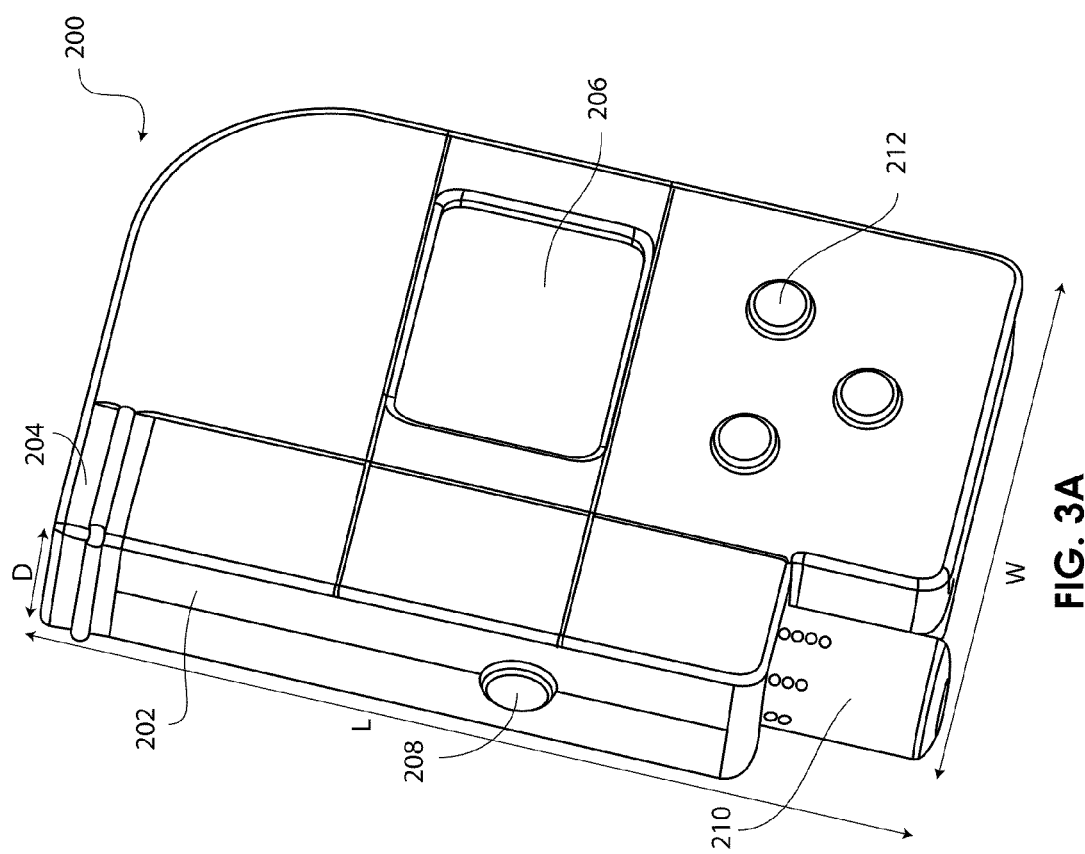

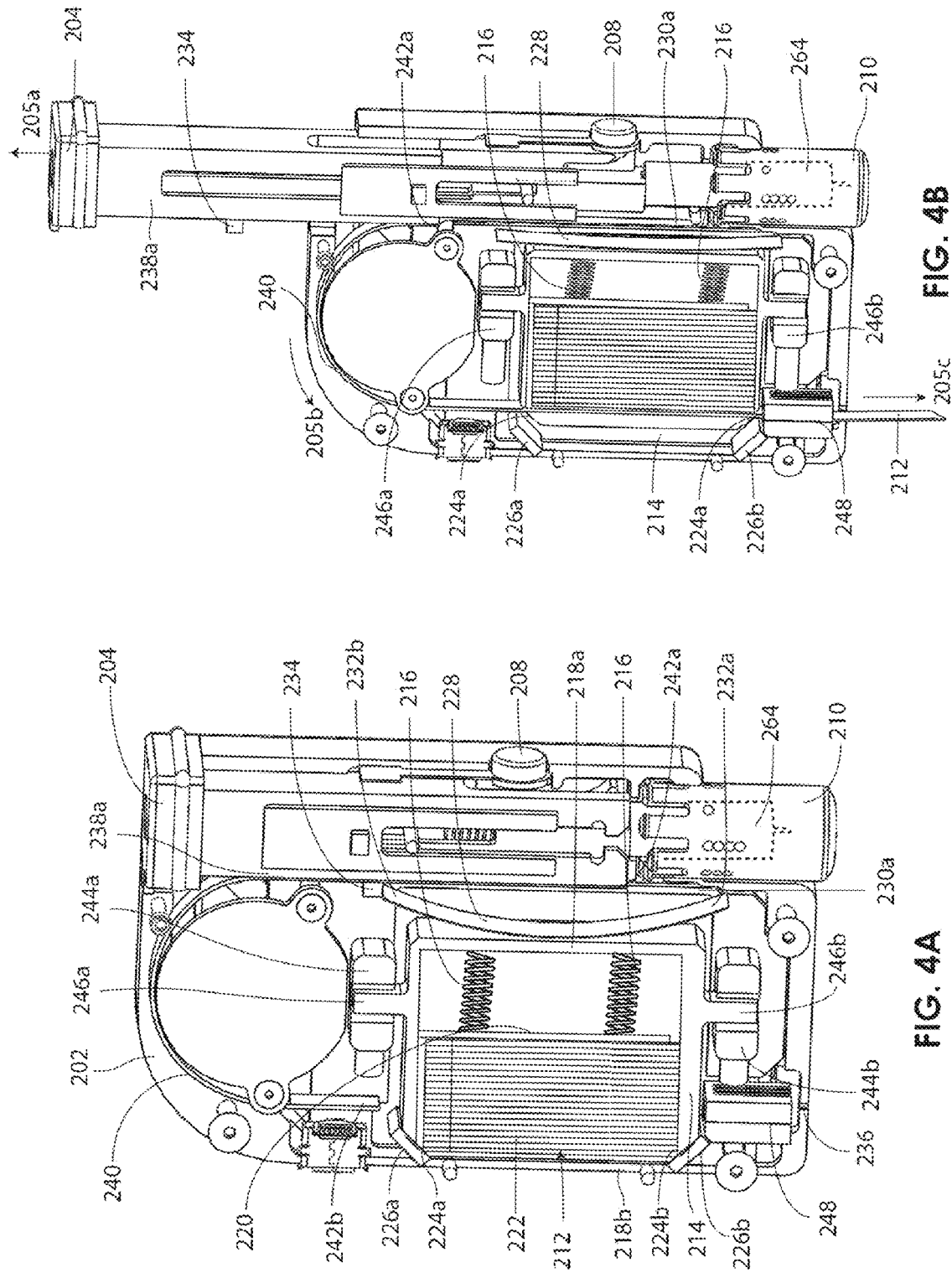

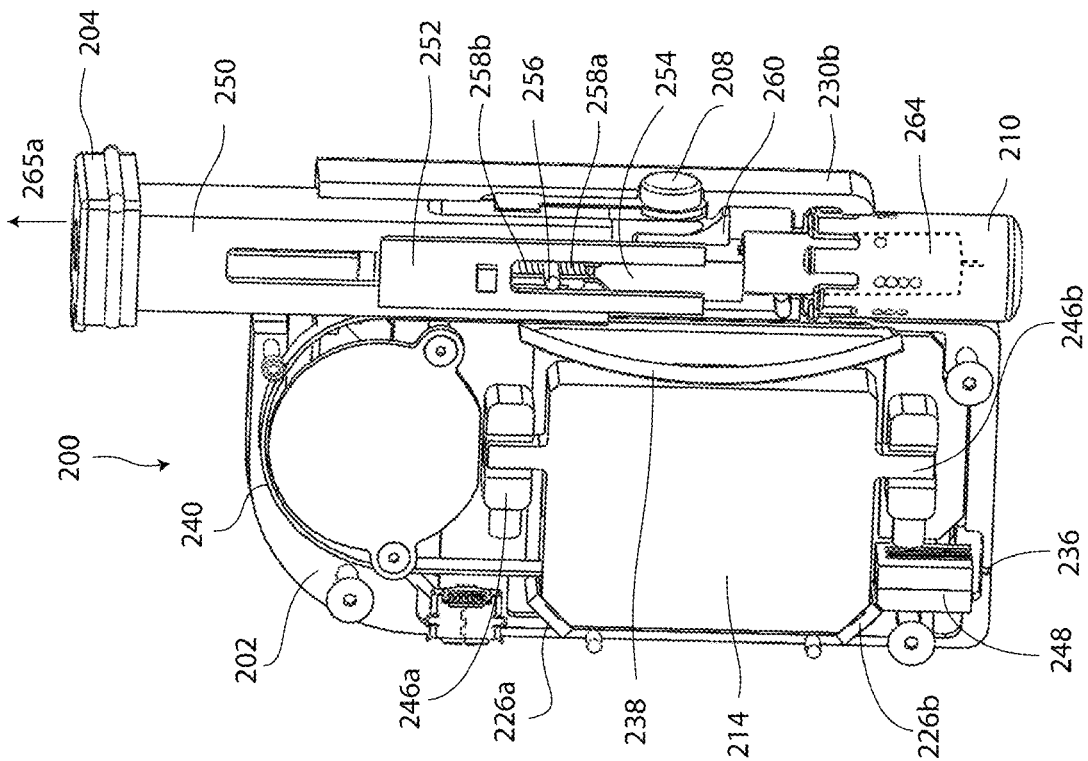
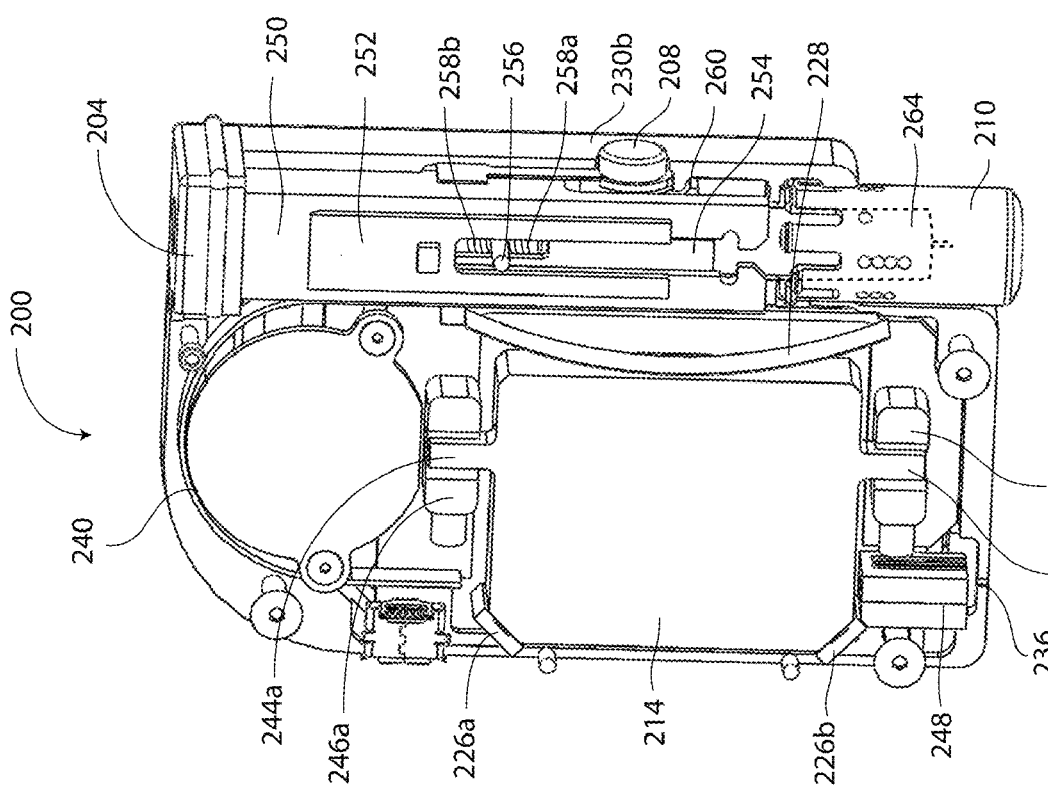

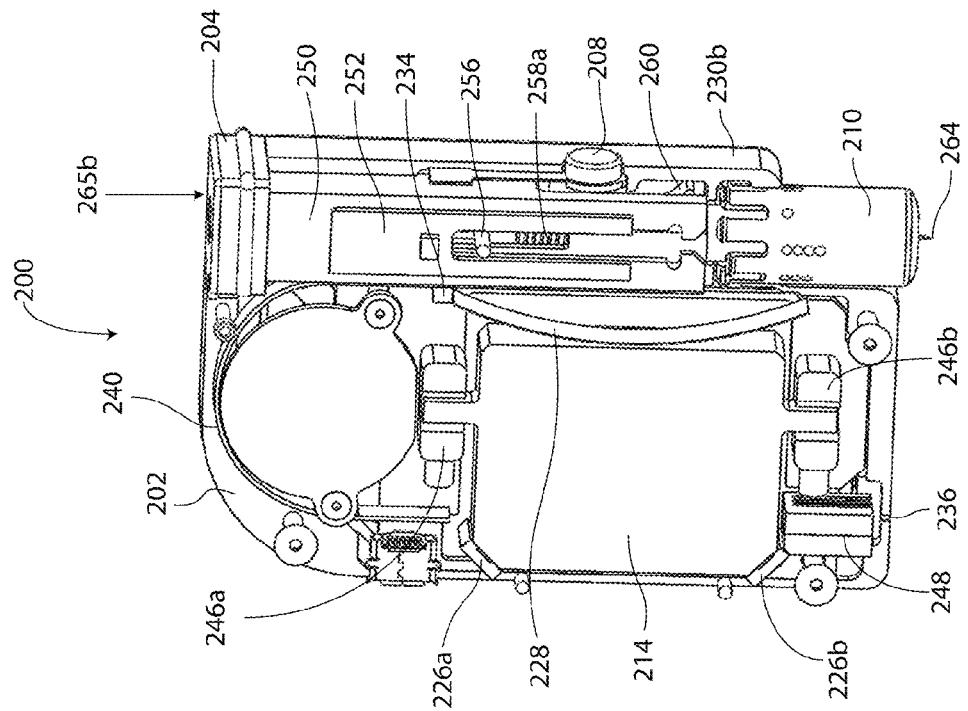
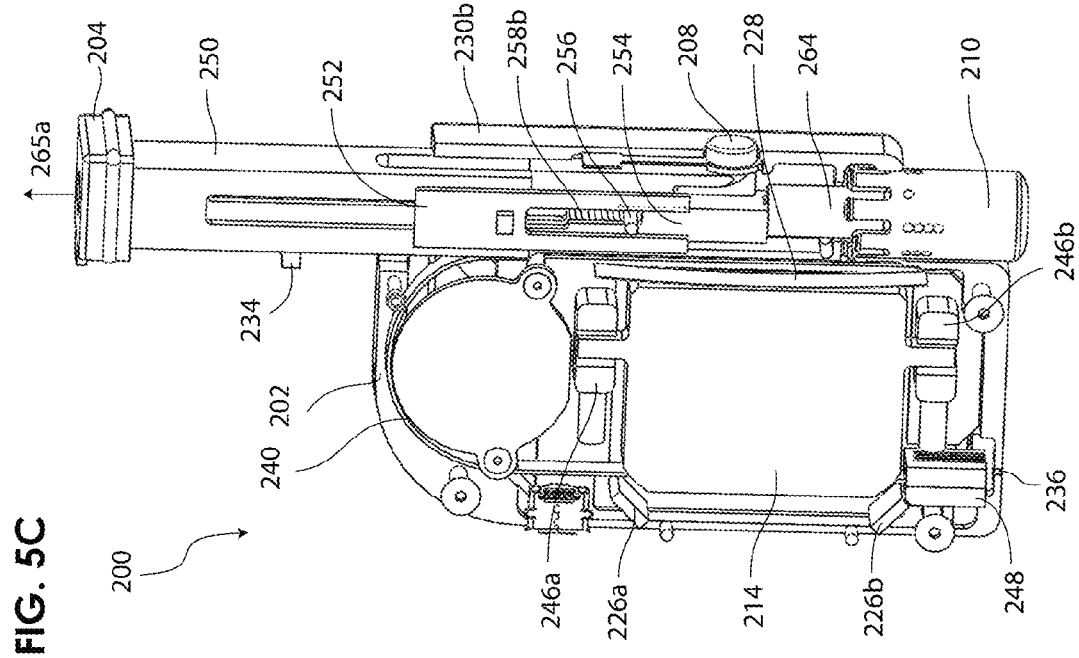
FIG. 5C
FIG. 5D

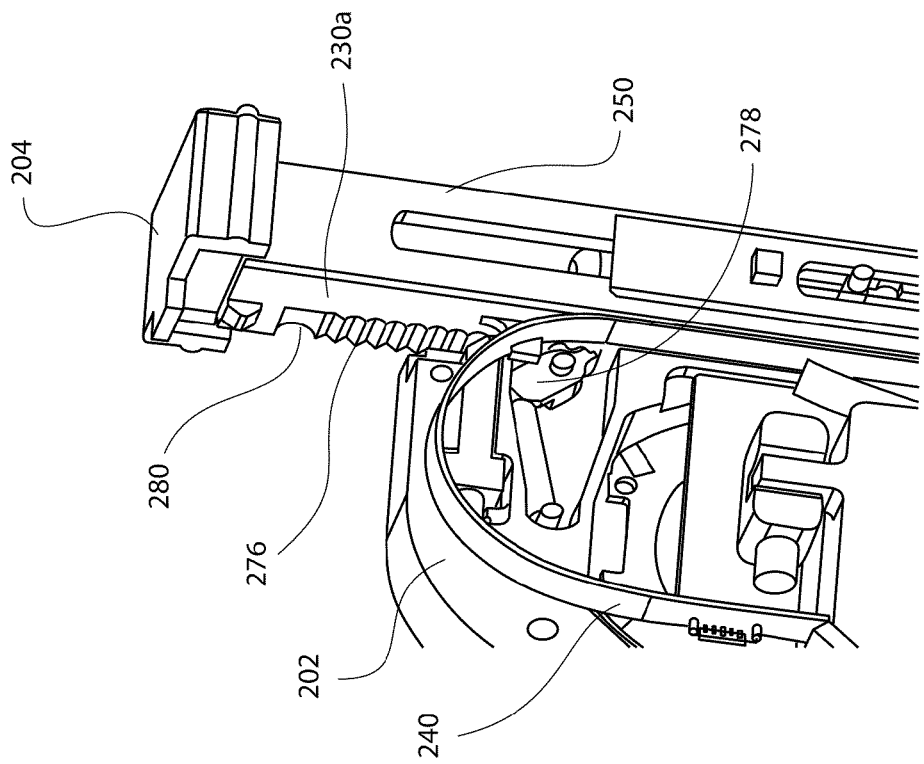
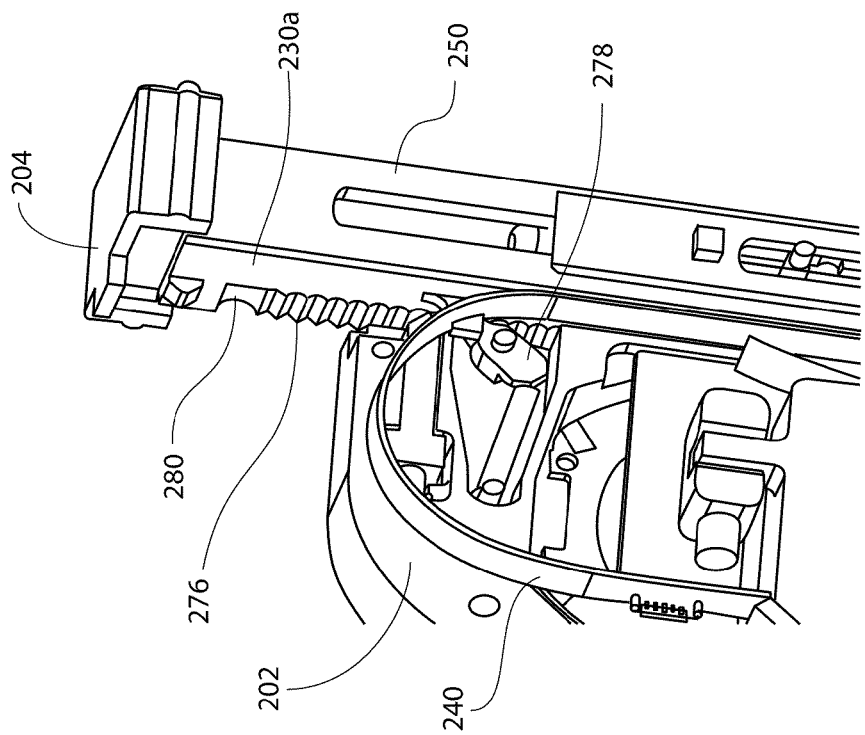

INTEGRATED LANCET AND ANALYTE TESTING APPARATUS

CROSS REFERENCE TO RELATED APPLICATIONS

This application claims the benefit of U.S. Provisional Patent Application Ser. No. 61/102,640 filed on Oct. 3, 2008, which is hereby incorporated by reference in its entirety.

BACKGROUND OF THE INVENTION

There are a number of instances when it is desirable or necessary to test or monitor the concentration of an analyte, such as glucose, lactate, or oxygen, for example, in bodily fluid of a body. Bodily sample analyte tests are routinely conducted in a variety of medical settings (e.g., doctor's office, clinic, hospital, by medical personnel) and in the home by the patient and/or a caretaker. For example, it may be desirable to monitor high or low levels of glucose in blood or other bodily fluid that may be detrimental to a human. In a healthy human, the concentration of glucose in the blood is maintained between about 0.8 and about 1.2 mg/mL by a variety of hormones, such as insulin and glucagons, for example. If the blood glucose level is raised above its normal level, hyperglycemia develops and attendant symptoms may result. If the blood glucose concentration falls below its normal level, hypoglycemia develops and attendant symptoms, such as neurological and other symptoms, may result. Both hyperglycemia and hypoglycemia may result in death if untreated. Maintaining blood glucose at an appropriate concentration is thus a desirable or necessary part of treating a person who is physiologically unable to do so unaided, such as a person who is afflicted with diabetes mellitus.

The most important factor for reducing diabetes-associated complications is the maintenance of an appropriate level of glucose in the blood stream. The maintenance of the appropriate level of glucose in the blood stream may prevent and even reverse some of the effects of diabetes. Certain compounds may be administered to increase or decrease the concentration of blood glucose in a body. By way of example, insulin can be administered to a person in a variety of ways, such as through injection, for example, to decrease that person's blood glucose concentration. Further by way of example, glucose may be administered to a person in a variety of ways, such as directly, through injection or administration of an intravenous solution, for example, or indirectly, through ingestion of certain foods or drinks, for example, to increase that person's blood glucose level.

Regardless of the type of adjustment used, it is typically desirable or necessary to determine a person's blood glucose concentration before making an appropriate adjustment. Typically, blood glucose concentrations are tested in vitro by the diabetic, or sometimes by a physician, periodically and often multiple times each day.

The tools typically used in conventional in vitro self-monitoring of blood glucose levels includes a lancing device having a removable and replaceable cap, a glucose meter, and a container or vial of glucose testing strips. The blood sample is obtained by using the lancing device, for example, to make blood available external to the skin, to obtain the necessary sample volume for in vitro testing. The fresh blood sample is then applied to an in vitro sensor, such as an analyte test strip, which is positioned in the meter, whereupon suitable detection methods, such as calorimetric, electrochemical, or photometric detection methods, for example, may be used to determine the person's actual blood glucose level. Such a glucose monitoring regime typically involves multiple steps, including: (1) locating and opening a test strip vial; (2) removing a test strip and replacing the lid on the vial; (3) inserting the test strip into the meter; (4) coding/calibrating the meter; (5) priming the lancing device; (6) lancing the finger or alternate site; (7) applying blood to the test strip; (8) waiting for the meter to analyze the blood glucose level and provide the test results; and (9) disposing of the used test strip. While such a regime is very effective, the use of a separate glucose meter, lancet and testing strips can be labor intensive and inconvenient. Additionally, with three separate components, use and handling of the system is more cumbersome and requires keeping track of and maintaining multiple components. Moreover, the extensive manual manipulations of such a regime and system make the process susceptible to user error.

As such, analyte meters having lancet mechanism and test strips integrated in a single unit or housing are highly desirable. With such a system, numerous analyte tests may be performed without having to manually load a new test strip for each test performed, or without having to separately handle a lancing device. However, a disadvantage of currently available integrated lancing and testing devices is that they tend to be bulky and relatively heavy, particularly if one or more motors, including one or more batteries sufficient to power the motors, are used to actuate the lancing mechanism and/or to advance a test strip into position to receive a body fluid sample.

Accordingly, it is desirable to have an integrated analyte measurement system which is easy to use and requires minimal steps each time a person tests his or her analyte level (e.g., a person with diabetes tests his or her glucose level), while not sacrificing accuracy, reliability or functionality.

SUMMARY OF THE INVENTION

Integrated lancing and analyte measurement systems are provided which minimize the number of actions required to operate the systems, accomplished in part by combining two or more user steps into one. Such integrated systems may be configured for making a blood glucose measurement with a single, complete manual actuation performed by the user. Such manual actuation may comprise any one or more of the movement of a handle or lever or the pressing of a button or the like. Methods of using the subject system are also provided.

These and other objects, advantages, and features of the invention will become apparent to those persons skilled in the art upon reading the details of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIGS. 1A-1C are perspective, front and back views, respectively, of an embodiment of an integrated lancing and analyte testing system of the present invention;

FIGS. 2A-2C are front and cutaway views, respectively, of the integrated system of FIGS. 1A-1C in various states of operation;

FIGS. 3A and 3B are front and back perspective views, respectively, of another integrated lancing and analyte testing system of the present invention;

FIGS. 4A and 4B are back cutaway views of the system of FIGS. 3A and 3B in neutral and test strip dispensed states, respectively;

FIGS. 5A-5D are back cutaway views of various component actions in firing of the lancet of the system of FIGS. 3A and 3B;

FIGS. 8A-8C are back cutaway views of the system of FIGS. 3A and 3B illustrating anti-jamming and one-way locking mechanisms of the system, with FIG. 8A providing an enlarged view of the subject mechanisms.

DETAILED DESCRIPTION OF THE EMBODIMENTS

Figure 6B:
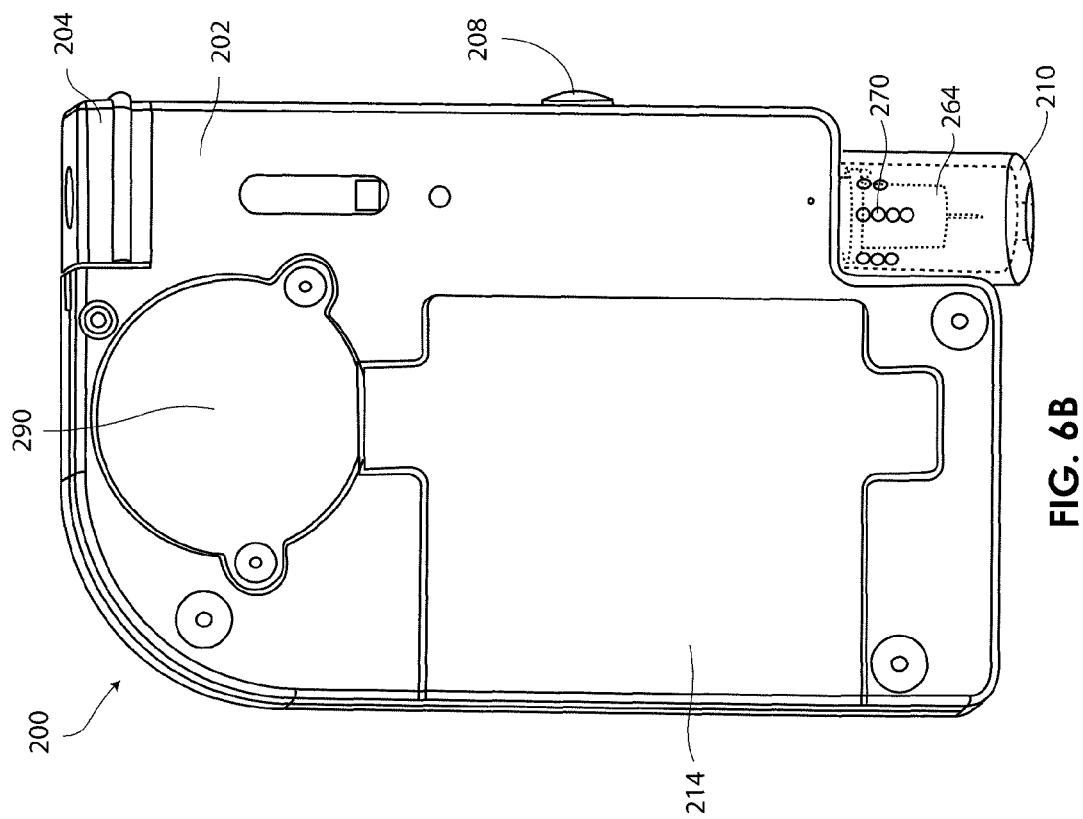
FIGS. 6A and 6B are back views of the system of FIGS. 3A and 3B illustrating exemplary positions of the system's lancet depth adjustment mechanism.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

As used herein and in the appended claims, the singular forms "a," "and," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The invention is now described in greater detail with respect to the exemplary embodiments of FIGS. 1 and 2 and FIGS. 3-8, respectively, which illustrate integrated lancing and analyte measurement systems which combine a blood analyte meter, a disposable cartridge of analyte, e.g., glucose or a ketone body, test strips, and a lancing mechanism in a single portable device. The particular system embodiments described herein are particularly suitable for blood glucose measurement applications, and thus, the following description is directed to such application; however, the present invention may be used in any analyte measurement application. Analyte sensors of this type are available from Abbott Diabetes Care Inc., Alameda, Calif. and include FreeStyle® and FreeStyle Lite™ test strips.

In addition to the embodiments specifically disclosed herein, the integrated systems described herein can be configured to work with a wide variety of analyte sensors, e.g., those disclosed in U.S. patent application Ser. No. 11/461,725, filed Aug. 1, 2006; U.S. Patent Application Publication No. 2007/0095661; U.S. Patent Application Publication No. 2006/0091006; U.S. Patent Application Publication No. 2006/0025662; U.S. Patent Application Publication No. 2008/0267823; U.S. Patent Application Publication No. 2007/0108048; U.S. Patent Application Publication No. 2008/0102441; U.S. Patent Application Publication No. 2008/0066305; U.S. Patent Application Publication No. 2007/0199818; U.S. Patent Application Publication No. 2008/0148873; U.S. Patent Application Publication No. 2007/0068807; U.S. Pat. No. 6,616,819; U.S. Pat. No. 6,143,164; and U.S. Pat. No. 6,592,745; the disclosures of each of which are incorporated by reference herein.

Analyte analysis may be performed by a variety of methods including, for example, amperometry, coulometry, potentiometry, and/or voltametry, including square wave voltametry.

Referring now to FIGS. 1A-1C, integrated lancing and analyte measurement system 100 includes a housing 102 which contains therein various assemblies of mechanical and electronic components, including but not limited to various components for directly interfacing with a lancet mechanism and an analyte test strip cartridge 114 (see FIG. 1C). Such interfacing includes individually translating the analyte test strips contained within a cartridge 114, coupled within housing 102, to a position at least partially outside housing 102 for sampling and testing of body fluid. The electronic components include various printed circuit boards having circuitry for storing electronic data and running software programs for controlling and operating the device and measuring the target analyte in the extracted bodily fluid.

Housing 102 further frames a display 106, such as an LCD screen, which provides visual information to the user including, but not limited to, glucose test values, instructions for performing a glucose measurement test with the system, prepping the meter for use, calibration information, and/or one or historical data relating to past tests or activities of the user that may affect his or her glucose level. The information provided on display 106 may be interactively accessed and manipulated by the user for assisting the user in his or her self-care regimen. Other visual, audible and/or touch sensitive mechanism for informing the user of measured glucose levels and other information regarding the user's self-care regimen may be provided. For example, words or alarms may be output audibly by the meter and/or the meter may vibrate.

System 100 provides various user-activated actuators for performing the various lancing and analyte testing functions of the meter, described in greater detail below with reference to FIGS. 2A-2C. A manual actuator or handle 104 (shown in FIGS. 1A-1C in a closed or down position), for example, primes or arms the lancing mechanism and advances a test strip from test strip cartridge 114. After the lancet is armed, a lancet firing button 108 is used to advance the lancet through an aperture (not visible) within an expression cap 110 at a relatively high rate of speed. When the lancet is fired, it protrudes through the aperture in the cap 110 and into the user's finger (or other body area), thereby extracting blood from the skin. Expression cap 110 may be particularly configured for engaging with a finger or other lancing site on the user's body to facilitate the expression of bodily fluid, e.g., blood, from the skin. The vertical height of expression cap 110 may be adjustable relative to the lancet when in a lancing position, described in greater detail with reference to the embodiment of FIGS. 6A and 6B. Alternatively, housing 102 may be configured to couple with one or more expression caps having varying heights.

FIGS. 1A-1C also show a test strip 112 extending from the distal end of housing 102 ready for sampling and testing of expressed bodily fluid. Test strip 112 may have been provided within disposable cartridge 114 (see FIG. 1C) operatively positioned within housing 102 and then fed-through the housing 102 by mechanisms provided therein, which are illustrated and described in more detail with reference to FIGS. 2A-2C. Cartridge 114 is sealed so as to maintain the functional integrity of the contained test strips. In alternate embodiments of the subject systems (not illustrated), the system is configured to receive a test strip inserted from external to the housing into a strip receiving port within the housing or forming part of the housing. In either embodiment, each test strip 112 includes one or more chemical reagents designed to interact with a target analyte(s) in body fluid applied to it in such a way that an analyte meter connected to electrodes of the test strip can derive a value of the level of the target analyte contained in the body fluid.

Referring now to FIGS. 2A-2C, the functionality of system 100 is described in greater detail. As mentioned above, system 100 integrally houses a lancing mechanism or sub-assembly 116 and an analyte sampling and testing sub-assembly (also simply referred to as a "meter") 126 provided in single, compact unit. The lancing mechanism 116 performs various functions including retaining one or more unused lancets, arming/or priming an individual lancet 128 for firing, and then advancing the armed lancet through a first aperture in the housing, i.e., within expression cap 110, to lance the skin of a user. The analyte sampling and testing sub-assembly/meter 126 functions to hold a plurality, e.g., 25 or more, of unused test strips 130, i.e., within cartridge 114, to advance a single test strip at a time through a second aperture within the housing, and to sample and test a target analyte concentration within bodily fluid extracted by the system's lancet. Both sets of functions, i.e., lancing and testing, are initiated by manual actuation of handle 104 which is affixed to two shafts extending perpendicularly from the bottom surface thereof—a lancet arming shaft 118 and a strip advance shaft 120—each of which is slidably translatable within respective lumens within housing 102. More specifically, the system is configured such that vertical translation 105 (see FIG. 2A) of handle 104 both arms the lancet to a trigger-actuated firing position and advances a distal or fluid-sampling end of a single test strip 112 from cartridge 114 and outside housing 102. A complete vertical translation sequence of handle 104 comprises pulling the handle away from the meter body 102 (as shown in FIG. 2B), followed by pushing the handle back toward and engaged against meter body 102 (as shown in FIG. 2C). As such, both shafts 118 and 120 are moved in parallel with a single motion of handle 104, yet perform separate functions simultaneously or in sequence with or without some temporal overlap.

The mechanical componentry and functionality of the two sub-systems is now described with respect to FIGS. 2B and 2C. Lancing mechanism 116 includes a lance carriage 124 which carries one or more lancets 128 at a distal end thereof and houses a compression spring mechanism having one or more compression springs (not visible). A linkage component 122 couples lancet carriage 124 to lance arming shaft 118. The spring mechanism is configured such that when handle 104 is pulled in the direction of arrow 115, as shown in FIG. 2B, lance arming shaft 118 moves linkage 122 upward, thereby stretching and/or compressing the one or more enclosed springs to place lancet 128 in armed state, i.e., biasing the lancet toward expression cap 110. Depressing lance firing button 108 (which may be performed prior to returning handle 104 to its down or seated position) releases the spring bias to advance lancet 128 through aperture 110 to lance a user's finger or alternate site disposed just outside expression cap 110. U.S. Pat. No. 6,283,982, which is assigned to the assignee hereof and incorporated herein by reference, discloses in greater detail exemplary lancing mechanisms which may be used with the integrated systems of the present invention.

Referring again to FIG. 2B, this same pulling action of handle 104 also brings a shoulder or distal surface 134 of strip advance shaft 120 into position at a proximal or top end of cartridge 114 such that shoulder 134 catches at a proximal end of the foremost testing strip 112 within cartridge 114. In order to preserve the sterility of test strips within the cartridge, a liner or coating may be provided between strip advance shaft 120 and its lumen to hermetically seal the proximal end of cartridge 114 while not hindering movement of the shaft within the lumen. Additionally, the distal end of shaft 120 may be coated or otherwise configured to sealably extend into the cartridge. Meanwhile, a strip advance mechanism, such as a spring 132, within cartridge 114 biases the enclosed stack 130 of test strips to axially align foremost strip 112 (i.e., the right-most strip in the figure) with a strip-dispensing aperture 138 at a distal end of cartridge 114.

As shown in FIG. 2C, upon pushing handle 104 down in the direction of arrow 125, shaft 120 advances test strip 112 a selected distance such that the distal testing end of strip 112 is exposed from housing 102. Aperture 138, in turn, may extend into a feed-through strip connector or holder 136 which is configured to physically align and electrically couple the strip electrodes with multiple complementary electrodes coupled to the meter's electronics. Feed-through path 136 may be integrated within or with housing 102 or may be provided as a separate component or connector which is removable (and replaceable) from housing 102. Both aperture 138 and connector 136 may be configured to maintain a hermetic seal at the strip dispensing end of cartridge 114. Additionally, as previously mentioned, feed-through path or connector 136 may be configured to receive a single testing strip from outside the housing 102 in the opposite direction of advancement of a strip from cartridge 114. Alternatively, a feed-through strip holder may be provided which simply holds, but does not make electrical contact with, the strip. Such a holder may be used for an optical measurement, which does not require electrical contact.

The system's electronics (including but not limited to electrodes, current and/or voltage meter, a processor, and a small battery for powering them) may be configured to automatically turn on when a strip 112 is positioned within feed-through pathway or connector 136. Then, momentarily after application of body fluid (already extracted by lancing mechanism 116) to the exposed end of strip 112, an electrochemical test of the sample fluid is performed and the measured analyte level appears on display 106. An electronic communications port (not shown) may also be provided by which a microprocessor housed within system 100 is accessed for programming, software download and off-board control.

Thus, in accordance with the embodiment of FIGS. 1 and 2, a single complete actuation of a handle, including pulling the handle out of the housing and pushing the handle back into the housing, arms the lancet and advances a single test strip from within a cartridge and provides it an exposed, test-ready position. The single actuation of the handle may also serve to turn on the meter, or the meter may be turned on by actuation of a separate switch or by placing a testing strip into a strip receiving port from outside of the housing.

Referring now to FIGS. 3-8, another exemplary embodiment of an integrated lancing and analyte measurement system 200 of the present invention is illustrated and described. As shown in FIGS. 3A and 3B, similar to system 100 of FIGS. 1 and 2, system 200 is provided in a compact housing 202 which frames a display 206 having functionality similar to that described above, has an expression cap 210 extending from the distal end of the housing about an aperture from which the lancet is advanced, and provides a manual actuator, handle or lever 204 and a lancet trigger button 208, the latter of which serve the similar functions of advancing a spring-loaded test strip from the internal test strip cartridge 214 as well as arming and firing the lancet, but accomplish such with different mechanisms and structures. Also unlike system 100, system 200 provides navigation keys 212 which enable a user to interface with and operate the system more interactively. Other variations between the two systems will become apparent from the following description.

Referring to the cutaway views of FIGS. 4A and 4B, another difference of system 200 from system 110 is in the configuration of strip cartridge 214, which is both internally and externally spring-loaded. As shown in FIG. 4A, an internal spring mechanism includes a pair of parallel compression springs 216 (although only one may be employed) extending between a side wall 218a of cartridge 214 and a compression bar 220, which in turn sandwiches a plurality of test strips 222, e.g., 25 or more, against an opposing side wall 218b of the cartridge. The placement of the springs 216 and use of compression bar 220 ensure an even force distribution across the length of the strips such that the foremost test strip 212 within the cartridge (i.e., the leftmost strip in the figure) is properly aligned with both a proximal aperture 224a and a distal aperture 224b within the proximal and distal walls, respectively, of cartridge 214. When cartridge is in a neutral or inactive position, as it is in FIG. 4A, cartridge apertures 224a, 224b are releasably sealed against sealing members or pads 226a, 226b, respectively. The sealing pads may be made of an elastomeric material which is soft enough to sufficiently seal against the cartridge apertures. The elastomeric material may also have very low water vapor transmission properties to prevent water vapor from diffusing through the pads. One exemplary material suitable for use with the present invention includes ethylene propylene diene M-class (EPDM).

As mentioned above, cartridge 214 is also externally biased—by two opposing spring mechanisms. An active or primary spring mechanism includes spring blocks 244a, 224b positioned on protrusions 246a, 246b extending from opposing ends of cartridge 214 which bias cartridge 214 away from sealing pads 226a, 226b (i.e., toward the right in the figure). A passive or secondary spring mechanism, such as a leaf spring 228, positioned between side wall 218a of the cartridge and internal wall 230 of the device, overrides the primary spring bias when cartridge 214 is in a neutral or inactive state. This override is accomplished by affixing a proximal end 232a of leaf spring 228 to internal wall 230a of housing 202 and allowing the distal or free end 232b of the leaf spring to abut a shoulder 234 extending from an inner wall 238a of pull lever 204. The opposing spring force provided by leaf spring 228 is greater than that of the primary spring mechanism 244 and, as such, in the neutral/inactive cartridge position of FIG. 4A, leaf spring 228 biases cartridge 214 against sealing pads 226a, 226b (i.e., toward the left in the figure) maintaining apertures 224a, 224b in a sealed condition. When lever 204 is pulled outward from housing 202, as indicated by arrow 205a in FIG. 4B, shoulder 234 is moved away from the free end 232b of leaf spring 228, thereby releasing the secondary bias on cartridge 214 and allowing the primary spring bias provided by springs 224a, 224b to take over and move cartridge 214 away from sealing pads 226a, 226b (i.e., toward the right in the figure).

The same action that unseals cartridge apertures 224a, 224b also dispenses a single test strip 212 from within cartridge 214 to outside housing 202 for fluid sampling. Such test strip dispensing is accomplished by a test strip pusher mechanism 240 in the form of a flexible strip, which may be made of one or more of various types of plastics, spring steel or braided steel cable, etc. Pusher strip 240 has a proximal end 242a affixed to inner wall 238a of pull lever 204 and a distal or free end 242b axially aligned to be received within aperture 224a when the aperture is unsealed, as shown in FIG. 4B. A length of pusher strip 240 slidably extends within a guide track or groove (not shown) within the housing body 202. When lever 204 is pulled in the direction of arrow 205a, fixed end 242a of pusher 240 rides along with the lever, and a length of pusher 240 is caused to travel counter-clockwise in the direction of arrow 205b causing free end 242b to enter into cartridge aperture 223a and thereby advance a single test strip 212 out of cartridge aperture 224b in the arcuate direction of arrow 205c. Upon exiting the cartridge, the distal or fluid-sampling end of test strip 212 is advanced through a feed-through connector or holder 48 and is exposed from lancing port 236. As with feed-through connector 136 of system 100 of FIGS. 1 and 2, feed-through path or track or connector 248 has electrical contacts for electrically coupling the test strip electrodes to the meter electronics (not shown). In certain embodiments 248 is a smart-sensor port as described in U.S. patent application Ser. No. 12/431,672 filed on Apr. 28, 2009, the disclosure of which is hereby incorporated by reference in its entirety.

Referring now to FIGS. 5A-5D, the operational sequence of the lancing mechanism of system 200 is now described. In the system's neutral position, as illustrated in FIG. 5A (and also FIG. 4A), lever 204 is in a closed or down position with its various components in an axially nested configuration. These components include a lever shaft housing 250 which slidably retains a rearming mechanism 252 (described in greater detail below with reference to FIGS. 7A and 7B), a lancet carriage or drive piston 254, and a lancet 264 (concealed within expression cap 210) which is carried on the distal end of lancet carriage 254. Extending radially from a distal end of the external wall of lancet carriage 254 is a ramped surface or foot 260. A dowel pin 256, one end of which is affixed to an internal back wall of shaft housing 250, extends transversely within the lancing mechanism, specifically through a slot or window within each of shaft 250, rearming mechanism 252, and lancet carriage 254. Pin 256 is further transversely positioned between the facing ends of two axially aligned compression springs 258a, 258b, which are nested within a hollow chamber within lancet carriage 254. As is explained below, spring 258a functions to provide a driving or firing force and spring 258b functions to provide a retraction or recoil force on the lancet immediately after firing of the lancet, with firing spring 258a having a much greater, e.g., up to about 100 times greater or more, spring constant than retraction spring 258b. As the position of dowel pin 256 is fixed, it remains stationary relative to the axial movement of the other lancing components during the lancing sequence and serves to sequentially compress each of the springs 258a, 258b at various points in the lancet armingfiring cycle, further described below. Positioned within and extending from an external wall 230b of lever 204 is a lancet firing button 208.

Upon initial pulling of lever 204 in the direction of arrow 265a, as illustrated in FIG. 5B, lancet carriage 254 is carried by shaft housing 250 in an upward direction, thereby compressing spring 258a and moving ramped surface 260 toward the underside of lancet firing button 208. Continued pulling of lever 204 in the direction of 265a to a fully-extended position, as illustrated in FIG. 5C, fully compresses spring 258a (not visible in FIG. 5C) and engages ramped surface 260 against the underside of button 208. The lancet mechanism is now fully armed and ready for on-demand firing by the user. To fire lancet 264, lancet firing button 208 is depressed which releases lancet carriage foot 260. The energy stored in compressed spring 258a is released thereby driving lancet carriage 254 downward and carrying shaft 250 along with it in the direction of arrow 265b, as shown FIG. 5D. Lancet carriage 254, in turn, drives lancet 264 through an aperture (not visible) within an expression cap 210 at a relatively high rate of speed and into the user's finger (or other body area), thereby extracting blood from the skin. This downward driving force, in turn, relaxes spring 258a and compresses 258b, which immediately retracts lancet carriage 254 back to a neutral position, completing the lancing sequence.

Figure 6A:
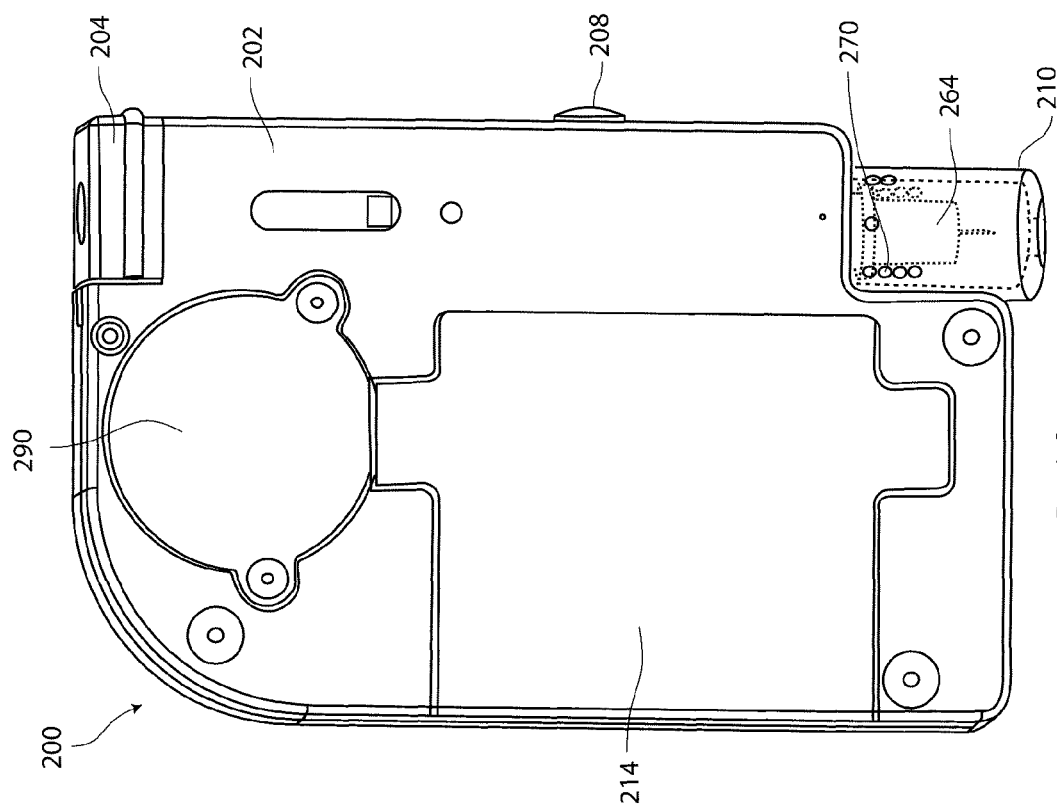

As illustrated in FIGS. 6A and 6B, the penetration depth of the lancet may be adjusted by adjusting the vertical height of expression cap 210, i.e., adjusting the axial extension of the cap beyond the distal end 202a of housing 202. As the lancing stroke of the lancet is fixed, adjusting the relative height of the expression cap 210 adjusts the location of the skin surface relative to the lance stroke, thereby allowing variable lancing depths to accommodate, for example, blood extraction at different sites on the body. Cap 210 may be slidably or rotatably coupled to a distal portion of housing 202 by means of a mating detent configuration or mating threaded configuration. The greater the exposed height or length of the cap 210 beyond the distal end 202a of housing 202, the shorter the lancing depth of the lancet. Indicia 270 such as lines or dots on the outer surface of cap 210 may be provided to indicate the lancing depth where the greater the number of exposed indicia 270, the shorter the lancing depth. For example, more dots 270 are exposed in FIG. 6A then in FIG. 6B indicating a shorter lancing depth in the former figure.

Figure 7B:
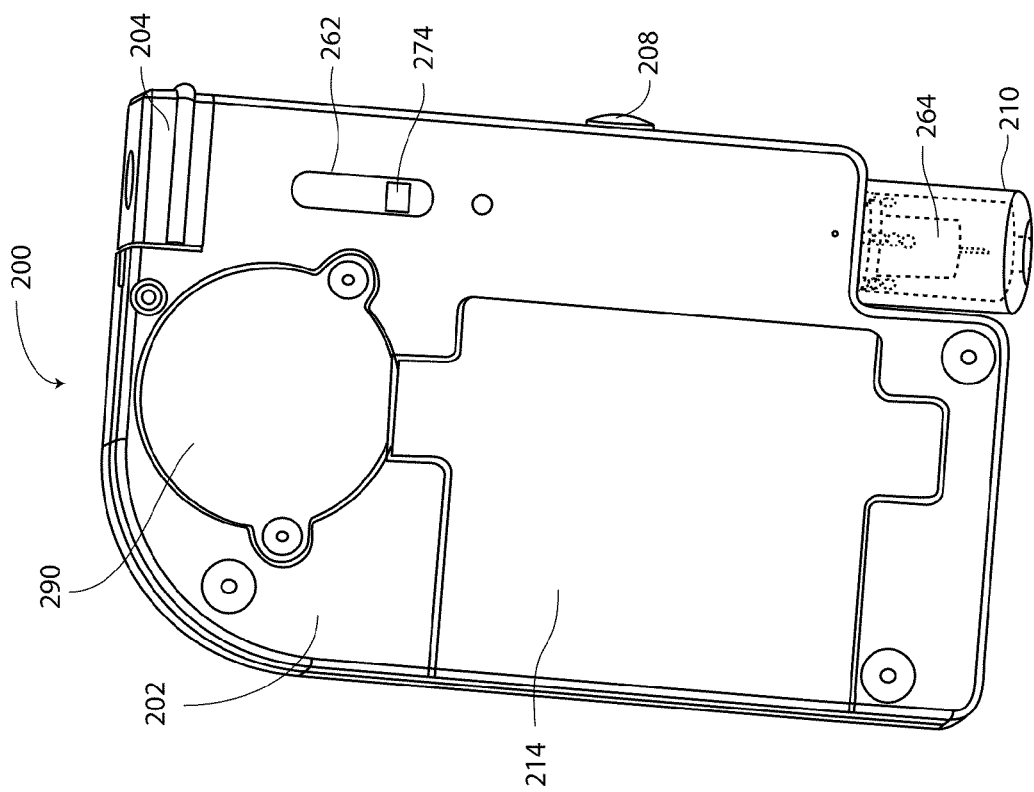
FIGS. 7A and 7B are back views of the system of FIGS. 3A and 3B illustrating rearming of the lancet mechanism.
Figure 7A:
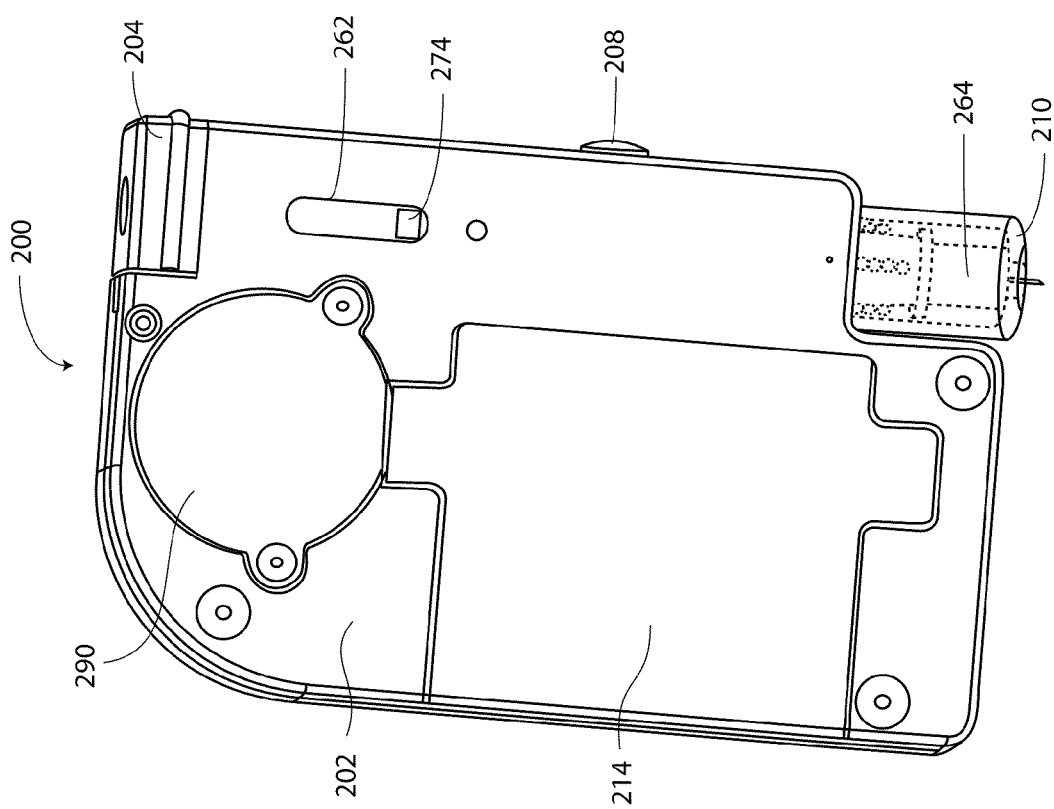

Another optional feature of system 200 is illustrated in FIGS. 7A and 7B in which a vertical window 262 is provided in the backside of housing 202 through which a lever or tab 274 slidably extends. Tab 274 extends from lancet rearming mechanism 252. Upon arming of lancet 264, as illustrated in FIG. 5C in which lever 204 is in a fully extended position, rearming lever 274 is automatically moved upward within window 262. Then, upon firing of the lancet 264, as shown in FIG. 5D, rearming slider 274 automatically returns to the distal most position, as illustrated in FIG. 7A. To rearm the lancet without dispensing another test strip (as is sometimes necessary if, upon the first lancing attempt, a sufficient amount of body fluid is not expressed), the user manually slides lever 274 upward, as illustrated in FIG. 7B. In this way, the driving and retraction springs (not shown) are extended and compressed, respectively, and the ramped foot (not shown) on the lancet piston is repositioned against the underside of lancet trigger button 208, thereby rearming the lancet piston.

Figure 8A:
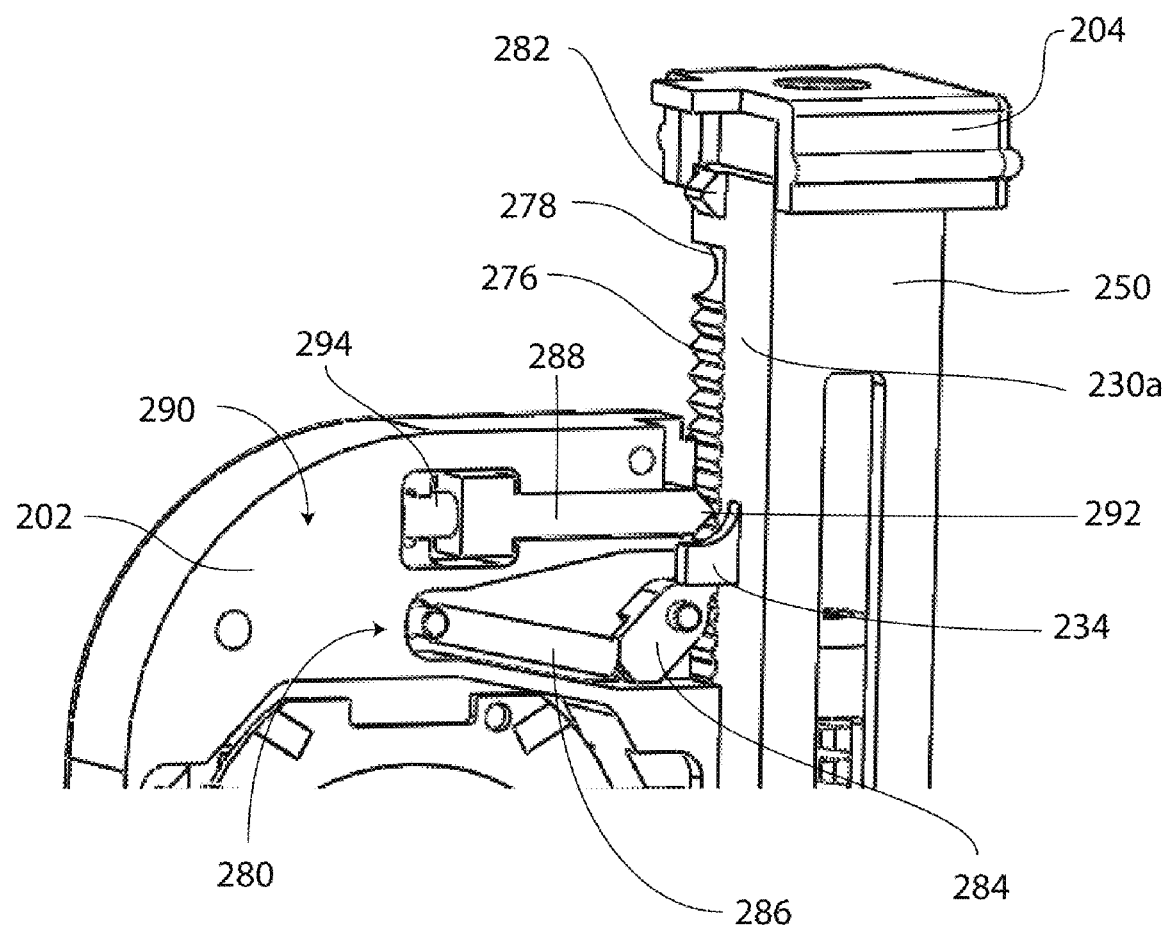

Yet another feature of system 200, as illustrated in FIGS. 8A-8C, is a mechanism which prevents lever arm 204 from jamming when being moved in/out or up/down during the test strip advancement and lancet arming and firing sequences. As best shown in FIG. 8A, the anti-jamming feature includes a one-way travel mechanism 280 in the form of a spring-loaded pawl gear 184 rotatably coupled to an extension spring 286. Pawl gear 284 engages with ratchet track 276 such that it allows only one-way movement of lever arm 204 once that movement is commenced. For example, when lever arm 204 is pulled upward from a neutral position (as shown in FIGS. 4A and 5A), i.e., in the direction of arrow 295a in FIG. 8B, pawl gear 285 is in a position relative to ratchet track 276 which, by the constant force placed on it by extension spring 286, only allows continued upward motion of lever arm 204, i.e., the lever cannot now be pushed back down. Upon full extension of lever arm 204 (as shown in FIG. 5C), the pawl 284 reaches and engages with an enlarged clearance 278 within ratchet track 276 (but at the opposite or lancing end of the track which is not visible from the views provided in the figures). This clearance 278 provides sufficient space for extension spring 286 to expand a bit further and thereby rotating pawl gear 284 within clearance 278. One-way travel mechanism 280, now facing the opposite direction, as illustrated in FIG. 8C, only allows lever arm 204 to be translated in the downward direction, as indicated by arrow 295b, to a fully retracted position. Stated a different way, the directionality of the pawl gear 284 can only reverse upon the pawl reaching a clearance 280 provided at each end of the ratchet track 276 within the lever side wall 230a (only the upper depression is visible in the figures). This configuration requires lever 204 to be fully extended (see directionality of pawl mechanism 284 in FIG. 8B) before being able to be pushed back into housing 202, and to be fully retracted (see directionality of pawl mechanism 284 in FIG. 8C) before being able to be pulled or extended.

Another feature of system 200, also illustrated in FIGS. 8A-8C, is a one-way locking mechanism 290 which insures proper sealing of strip cartridge 214 against sealing pads 226a and 226b by securing lever 204 into position when it is fully inserted into the meter. As best illustrated in FIG. 8A, this locking mechanism 290 includes a spring-loaded plunger 288 having a tapered distal end 292 that engages with striker block 282 on the wall of shaft housing 250 when lever 204 is fully inserted into the meter. A force is thus required to push striker block 282 past spring-loaded plunger 288 when moving lever 204 into or out of the fully inserted position. This prevents lever 204 from inadvertently moving out of the fully inserted position, for example by the force of leaf spring 228 which would compromise the seal of strip cartridge 214 against sealing pads 226a and 226b.

The integrated meters described herein, and those that are structurally and/or functionally equivalent, provide multiple advantages over conventional meters, not the least of which is the performance of various functions simultaneously or by means of a single action or operational sequence. The combined functionality and shared componentry of the lancing and strip dispensing mechanisms, and the absence of motors and large batteries, contribute to keeping the overall size of subject integrated meters smaller and lighter than other conventional integrated meters. For example, the length L of the subject meters of the present invention are in the range from about 2 to about 3 inches, and in one particular embodiment is about 2.75 inches. The width W of the meters is in the range from about 1.5 inches to about 2.5 inches and in one particular embodiment is about 2.0 inches, and its depth or thickness D is in the range from about 0.5 inch to about 1 inch, and in one particular embodiment is about 0.71 inch. While these numbers can change with different embodiments, they are generally far smaller than an integrated meter that includes one or more motors, with associated batteries, for actuating the lancet and/or for moving strips therein. The subject meters do include a battery, e.g., battery 290 in system 200, for powering the meter electronics, but such battery may be smaller and far less powerful than one that would be required to power one or more motors.

In alternative embodiments of the subject integrated systems, a handle or lever may be manually-actuated to arm the lancet, while a strip is fed to the meter from the outside into a strip receiving port. In another alternative embodiment, a handle or lever may be manually-actuated to remove a strip from an internal cartridge for performing a test, while a motor arms the lancet or a separate manual mechanism is used to arm the lancet. Also, a handle or lever may arm the lancet while a separate manual mechanism is used to move the strip into position for a test. Other mechanisms which may be used in lieu of handles or levers include bur are not limited to dials, wheels, levers, pins, racks, gears, pulleys, various springs, or other mechanical components that may be manually operated.

In some embodiments, the system is configured to perform medication dosage calculation functions, such as a single-dose calculation function for injection of rapid acting insulin and/or long acting insulin. Analyte meters which include medication dosage calculation functions and methods of performing the dosage calculation functions are described, for example, in U.S. patent application Ser. No. 11/396,182, filed Mar. 31, 2006, titled "Analyte Monitoring Devices and Methods Therefor," the disclosure of which is incorporated by reference herein. In one embodiment, the system is configured to perform a bolus calculation function. For example, the controller unit may be configured to determine a bolus dosage, e.g., an insulin bolus dosage, based on the signal received from the analyte sensor.

In some embodiments, the system 200 includes an optional communication device (not shown), e.g., a receiver and/or transmitter for communicating with another device, e.g., a medication delivery device and/or a patient monitoring device, e.g., a continuous glucose monitoring device as described above, or a health management system, such as the CoPilot™ system available from Abbott Diabetes Care Inc., Alameda, Calif. The communication device can be configured for wired or wireless communication, including, but not limited to, radio frequency (RF) communication, Zigbee communication protocols, WiFi, Bluetooth communication protocols, and cellular communication, such as code division multiple access (CDMA) or Global System for Mobile communications (GSM).

In one embodiment, system 200 includes a wireless communication device, wherein the wireless communication device is configured for bi-directional radio frequency (RF) communication with other devices to transmit and/or receive data to and from system 200.

In one embodiment, the communication device is configured to include physical ports or interfaces such as a USB port, an RS-232 port, or any other suitable electrical connection port to allow data communication between the system 200 and other external devices such as a computer terminal (for example, at a physician's office or in hospital environment), an external medical device, such as an infusion device or including an insulin delivery device, or other devices that are configured for similar complementary data communication.

In one embodiment, the communication device is configured for infrared communication, Bluetooth communication, or any other suitable wireless communication mechanism to enable the system 200 for communication with other devices such as infusion devices, analyte monitoring devices, computer terminals and/or networks, communication enabled mobile telephones, personal digital assistants, or any other communication devices which the patient or user of the analyte meter may use in conjunction therewith, in managing the treatment of a health condition, such as diabetes.

In one embodiment, the system 200 is configured to wirelessly communicate with a server device, e.g., using a common standard such as 802.11 or Bluetooth RF protocol, or an IrDA infrared protocol. The server device could be another portable device, such as a Personal Digital Assistant (PDA) or notebook computer, or a larger device such as a desktop computer, appliance, etc. In some embodiments, the server device has a display, such as a liquid crystal display (LCD), as well as an input device, such as buttons, a keyboard, mouse or touch-screen.

A variety of analyte meters are known in the art, many of which includes additional components and functionalities which can be readily incorporated into the analyte meters described herein. Disclosure of such additional components and functionalities can be found, for example, in U.S. Patent Application Publication No. 2008/0119702, U.S. Patent Application Publication No. US 2008/0114280, and U.S. Patent Application Publication No. 2008/0119710, the disclosure of each of which is incorporated by reference herein.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An integrated analyte measurement system, comprising:
a housing comprising a first end and a second end;
a lancet positionable within the housing for advancement through a first aperture in the first end of the housing;
electronics within the housing for measuring an analyte level within body fluid;
a feed-through path configured for retaining a test strip within a second aperture in the first end of the housing wherein the test strip is exposed for application of body fluid to the test strip, and for simultaneously electronically coupling the test strip with the electronics;
a pusher mechanism for pushing a test strip through the second aperture; and
a lever;
wherein the system is configured to arm the lancet for advancement with a single user action comprising translating the lever along a single axis of motion defined by the first and second ends of the housing; and
wherein the system is configured to push a test strip through the second aperture with the single user action, further comprising advancing the pusher mechanism in an arcuate manner within the housing such that the pusher mechanism advances the test strip in a direction opposite to that in which the lever is translated.

2. The system of claim 1, wherein the analyte test strip is sealably contained within the housing, and wherein the system is further configured to advance the test strip to within the feed-through path with the single user action.

3. The system of claim 2, further comprising a cartridge contained within the housing and configured for containing a plurality of analyte test strips in the cartridge, wherein the system is configured to advance a single test strip at a time from within the cartridge to within the feed-through path with the single user action.

4. The system of claim 3, wherein the cartridge comprises first and second openings, wherein the first opening is aligned with the second aperture within the housing, the system further comprising a pusher mechanism for entering the first opening and pushing a single test strip through the second opening.

5. The system of claim 4, wherein the pusher mechanism comprises a flexible strip.

6. The system of claim 5, wherein the pusher mechanism comprises a shaft.

7. The system of claim 4, wherein the first and second openings are sealable, and wherein the single user action unseals the openings.

8. The system of claim 3, wherein the plurality of test strips is biased against a wall of the cartridge.

9. The system of claim 8, wherein the test strips are biased by a spring mechanism contained within the cartridge.

10. The system of claim 4, wherein the cartridge is biased by a spring mechanism within the housing to seal the first and second openings.

11. The system of claim 10, wherein the single use action releases the bias on the cartridge thereby unsealing the first and second openings.

12. The system of claim 1, wherein the single user action comprises extending the lever away from the housing.

13. The system of claim 1, wherein a second single user action advances the lancet through the first aperture.

14. The system of claim 13, wherein the second single user action comprises pushing a button framed within the housing.

15. The system of claim 1, wherein the feed-through is integrated within the housing or is coupled to the housing.

16. The system of claim 1, wherein the feedthrough path comprises multiple electrodes for electronically coupling to corresponding electrodes on the test strip.

17. The system of claim 1, wherein the electronics are configured to turn on when a test strip is within the feed-through path.

18. The system of claim 1, wherein the system is configured to receive the analyte test strip within the feed-through path from outside the housing through the second aperture.

19. The system of claim 1, wherein the electronics are configured to optically measure an analyte level.

20. The system of claim 1, further comprising a lancing mechanism within the housing configured for arming and advancing the lancet, wherein the lancing mechanism comprises a firing spring and a return spring, wherein the firing spring has a greater spring constant than the return spring.

21. The system of claim 1, further comprising a manually activated lever, wherein the single user action comprises pulling the lever in a first direction.

22. The system of claim 21, wherein pulling the lever advances the test strip into the feed-through path.

23. The system of claim 21, further comprising a lancet firing button for moving the lever in an opposite direction and advancing the lancet through the first aperture.

24. The system of claim 21, wherein the single user action further comprises pushing the lever in an opposite direction.

25. The system of claim 24, wherein the lever is coupled to and drives a lance arming shaft and a strip advance shaft.

26. The system of claim 25, wherein the lance arming shaft and the strip advance shaft extend approximately in parallel from a bottom surface of the lever.

27. The system of claim 1, further comprising an expression cap coupled to the housing at the first aperture.

28. The system of claim 27, wherein the housing is configured to couple with one or more expression caps having various heights for varying a lancing depth.

29. The system of claim 27, wherein the height of the expression cap is adjustable to vary a lancing depth.

30. The system of claim 29, wherein the expression cap comprises indicia on an external surface indicative of the lancing depth.

31. The system of claim 21, further comprising a mechanism within the housing configured for preventing movement of the lever in a second direction until the lever has been fully extended in the first direction.

32. The system of claim 31, wherein the mechanism is further configured for preventing movement in the first direction upon commencement of movement in the second direction.

33. The system of claim 2, further comprising a mechanism for rearming the lancet without advancing a test strip.

* * * * *